United States Patent [19]

Suzuki et al.

[11] Patent Number: 5,011,973
[45] Date of Patent: Apr. 30, 1991

[54] NOVEL PROCESS FOR PRODUCING BISCHOLINE-DISULFONATE DERIVATIVES

[75] Inventors: Yasuyuki Suzuki; Noboru Takagawa; Mikio Kawabata; Mariko Hayashi; Akiko Takagi; Takako Wakamiya; Isamu Saikawa, all of Toyama, Japan

[73] Assignee: Toyama Chemical Co., Ltd., Tokyo, Japan

[21] Appl. No.: 352,610

[22] Filed: May 15, 1989

Related U.S. Application Data

[63] Continuation of Ser. No. 111,108, Oct. 20, 1987, abandoned, which is a continuation of Ser. No. 842,069, Feb. 20, 1986, abandoned, which is a continuation of Ser. No. 485,617, Apr. 18, 1983, abandoned.

[30] Foreign Application Priority Data

Apr. 19, 1982 [JP] Japan .................... 57-64075

[51] Int. Cl.$^5$ ............................. C07C 69/66
[52] U.S. Cl. ..................... 560/185; 564/293; 564/282
[58] Field of Search ............ 560/185; 564/293; 260/501.15

[56] References Cited

U.S. PATENT DOCUMENTS

| | | | |
|---|---|---|---|
| 2,810,720 | 10/1957 | Lane | 260/501.15 |
| 2,831,019 | 4/1958 | Erskine | 260/501.15 |
| 2,865,805 | 12/1958 | Frant et al. | 260/501.15 |
| 3,024,283 | 3/1962 | Metcalfe et al. | 564/296 |
| 3,069,321 | 12/1962 | Broh-Kahn et al. | 260/501.15 |
| 3,190,919 | 6/1965 | Swanson | 564/296 |
| 3,903,137 | 9/1975 | Miura et al. | 560/185 |

FOREIGN PATENT DOCUMENTS 563481 8/1944 United Kingdom .

OTHER PUBLICATIONS

Kirk-Othmer, *Encyclopedia of Chemical Technology* (1947), vol. 1, Interscience, Publ., pp. 333-334.
Kirk-Othmer, *Encyclopedia of Chemical Technology* (1966), vol. 8, Interscience, Publ., pp. 356-359.

Primary Examiner—Paul J. Killos
Attorney, Agent, or Firm—Jordan B. Bierman

[57] ABSTRACT

The process for producing bischoline-disulfonate derivatives of Formula (I)

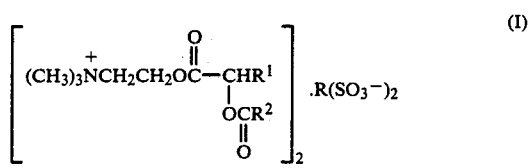

useful for enhancing the digestive function comprising reacting, in the presence of an organic solvent, a trimethylammonium salt derivative of Formula (II)

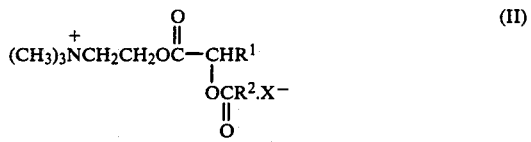

wherein $R^1$ and $R^2$ are individually lower alkyl and X is a group removable by a disulfonic acid of Formula (III)

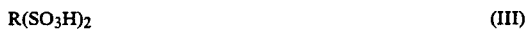

wherein R is a naphthylene, or an organic base salt of said acid.

9 Claims, No Drawings

NOVEL PROCESS FOR PRODUCING BISCHOLINE-DISULFONATE DERIVATIVES

This application is a continuation of application Ser. No. 111,108, filed Oct. 20, 1987 now abandoned which is a continuation of 842,069, filed Feb. 20, 1986, now abandoned which is a continuation of application Ser. No. 485,617, filed Apr. 18, 1983; now abandoned which, in turn, claims the priority of Japanese Application 64075/1982, filed Apr. 19, 1982.

This invention relates to a new process for the production of the bischoline-disulfonate derivative of Formula (I)

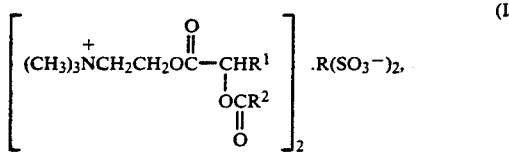

wherein each of $R^1$ and $R^2$ represents a lower alkyl group and R is a naphthylene. The compounds produced by the process of this invention find utility in enhancing the digestive function.

The known processes for producing choline-sulfonates are (1) acylating an α-hydroxy-α-alkylacetic acid trimethylammonioethyl ester sulfonate with an alkanoic acid derivative (Japanese Patent Publication 37334/1978), (2) acylating choline-sulfonate with the derivative of an α-alkonyloxy-α-alkylacetic acid (Japanese Patent Publication 21490/1977), and (3) reacting an α-acyloxy-α-alkylacetic acid dimethylaminoethyl ester with methylsulfonate (Japanese Patent Publication 1251/1980). These methods are also mentioned in U.S. Pat. No. 3,903,137.

An object of the present invention is to provide a new process for producing the compounds of Formula (I).

A second object of the invention is to produce bischoline-disulfonate derivative of Formula I in high yield and high purity.

According to the present invention, high yields of high purity bischoline-disulfonates of Formula I can be obtained by the reaction of a trimethylammonium salt of Formula (II)

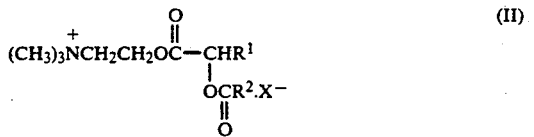

wherein X is a removable group, with a disulfonic acid of Formula (III)

$R(SO_3H)_2$     (III)

or an organic base salt thereof in the presence of an organic solvent. $R^1$ and $R^2$ are each lower alkyls having 1 to 5 carbon atoms; e.g. methyl, ethyl, propyl, butyl, pentyl, and the like.

X is any group which can be removed by a disulfonic acid of Formula (III) or the organic base salt thereof. More specifically, X includes: (1) halogen atoms, such as chlorine, bromine, iodine, and the like; (2) sulfonic acid residues, e.g. residues of alkanesulfonic acids such as methanesulfonic acid, ethanesulfonic acid, and the like; arylsulfonic acids such as benzenesulfonic acid, toluene-2-sulfonic acid, toluene-4-sulfonic acid, naphthalene-1-sulfonic acid, naphthalene-2-sulfonic acid, and the like; aralkanesulfonic acids, such as phenylmethanesulfonic acid and the like; cyclohexaminesulfonic acids; camphor-3-sulfonic acid; camphor-10-sulfonic acid, and the like; (3) alkylsulfuric acid residues, such as residues of methylsulfuric acid, ethylsulfuric acid, and the like; (4) alkylphosphate residues, such as residues of dimethylphosphate, and the like; and (5) any other acid residues removable by a disulfonic acid or a disulfonic acid organic base salt. Each of the above named residues differs from its parent acid in that it has one less hydrogen atom and, hence, carries a negative charge. Among the removable groups described above, it is preferable to use a halogen atom, a sulfonic acid residue, an alkylsulfuric acid residue or an alkylphosphate residue.

Any naphthylene-disulfonate or organic base thereof can be utilized as the disulfonic acid of Formula (III). These are exemplified by, but not limited to, naphthalene-1,5-disulfonic acid, naphthalene-2,6-disulfonic acid, naphthalene-2,7-disulfonic acid and the like. Hydrates of the naphthylene-disulfonates are also operable in the instant invention.

The trimethylammonium salt of Formula (II) can be obtained by methods know to persons of ordinary skill in the art.

The organic solvents which are suitable for use in the process of the present invention are not critical. Examples thereof are alcohols, such as ethanol, propanol, isopropanol, butanol, and the like; amides, such as N,N-dimethylformamide, N,N-dimethylacetamide, and the like; ethers, such as dioxane, tetrahydrofuran, and the like; ketones, such as acetone and the like; esters, such as ethyl acetate and the like; halogenated hydrocarbons, such as methylene chloride, chloroform, and the like; dimethylsulfoxide and the like. These solvents may be used individually or as mixtures. A preferred solvent is an alcohol or a mixture of an alcohol with other organic solvents. The most preferred solvents are ethanol or isopropanol.

Examples of the organic base portion of the disulfonic acid organic base salt are primary amines, such as methylamine, ethylamine, monoethanolamine, and the like; secondary amines, such as dimethylamine, diethylamine, and the like; and tertiary amines, such as trimethylamine, triethylamine, N-methylmorpholine, N-methylpiperidine, and the like. Among these salts, the preferred salt is a tertiary amine salt and, in particular, the triethylamine salt. The organic base salt of the disulfonic acid may be preformed or formed in situ.

The amount of solvent to be used is not critical. The ratio of solvent to Formula (II) compound is 4:1 to 20:1 on a volume to weight basis for example, volume in milliliters and weight in grams. It is also preferable that the Formula (II) compound be used in an amount of 1 chemical equivalent, or slight excess thereof, per equivalent of the disulfonic acid or disulfonic acid organic base salt.

There are no specific constraints on the reaction temperature or time; the reaction can be satisfactorily carried out at any temperature from about 5° C. to about 80° C., and the reaction time is conveniently about 5 minutes to about 2 hours.

According to the process of our invention, it is possible to obtain the desired compounds (those of Formula I) in surprisingly high purity and surprisingly high yield. The product is not contaminated with the starting materials or decomposition products. When alcohol is used as the solvent, the bischoline-disulfonate derivative obtained is also of high yield and high purity. Surprisingly, the expected side reactions, such as alcoholysis, do not occur.

The following Examples further illustrate, but do not limit, the invention.

EXAMPLE 1

4 g of α-acetoxy-α-methylacetic acid dimethylaminoethyl ester was dissolved in 15 ml of isopropanol and 4.1 g of p-toluenesulfonic acid methyl ester was added dropwise thereto. Thereafter, the reaction was carried out at 45° to 50° C. for 15 min., and the resultant mixture was cooled. Into this solution, 15 ml of an isopropanol solution containing 3.5 g of naphthalene-1,5-disulfonic acid tetrahydrate was added dropwise at 20° C.

After reacting for one hour, the precipitated crystals were collected by filtration, washed twice with 15 ml of isopropanol and then dried to obtain 6.87 g (yield 95%) of bis-(α-acetoxy-α-methylacetic acid trimethylammonioethyl ester) naphthalene-1,5-disulfonate having a melting point of 184° to 189° C.

These crystals were recrystallized from 95% ethanol, yielding purified crystals having a melting point of 190° to 192° C.

EXAMPLE 2

4 g of α-acetoxy-α-methylaminoethyl ester was dissolved in 15 ml of isopropanol. 2.7 g of dimethylsulfuric acid was added dropwise to the solution at room temperature, after which the reaction was carried out at 40° to 45° C. for 15 min. and the reaction mixture was cooled. Into this solution, 15 ml of an isopropanol solution containing 3.5 g of naphthalene-1,5-disulfonic acid tetrahydrate was added dropwise at 20° C.

After reacting for one hour, the precipitated crystals were collected by filtration, washed twice with 15 ml of isopropanol and then dried to obtain 6.8 g (yield 94.5%) of bis-(α-acetoxy-α-methylacetic acid trimethylammonioethyl ester) naphthalene-1,5-disulfonate having a melting point of 188° to 191° C.

These crystals were recrystallized from 95% ethanol yielding purified crystals having a melting point of 190° to 192° C.

EXAMPLE 3

To 25 ml of an isopropanol solution containing 5.0 g of α-acetoxy-α-methylacetic acid trimethylammonioethyl ester chloride, 25 ml of isopropanol solution containing 3.5 g of naphthalene-1,5-disulfonic acid tetrahydrate was added dropwise at 20° C. A seed crystal was added to this solution, after which the reaction was carried out with stirring at 20° C. for one hour.

The precipitated crystals were collected by filtration, washed twice with 15 ml of isopropanol, and then dried to obtain 6.75 g (yield 93.4%) of bis-(α-acetoxy-α-methylacetic acid trimethylammonioethyl ester) naphthalene-1,5-disulfonate having a melting point of 186° to 190° C.

These crystals were recrystallized from 97% ethanol, yielding purified crystals having a melting point of 190° to 192° C.

EXAMPLE 4

2.8 g of trimethylphosphate was added to 4 g of α-acetoxy-α-methyl-acetic acid dimethylaminoethyl ester. The mixture was reacted at 90° C. for 1.5 hours, and cooled. 15 ml of ethanol was added to the resulting α-acetoxy-α-methylacetic acid trimethylammonioethyl ester dimethylphosphorate, followed by the addition of 15 ml of ethanol containing 3.5 g of naphthalene-1,5-disulfonic acid tetrahydrate at 20° C.

After the reaction proceeded for one hour, the precipitated crystals were collected by filtration, washed twice with 15 ml of ethanol, and then dried to obtain 6.79 g (yield 94%) of bis-(α-acetoxy-α-methylacetic acid trimethylammonioethyl ester) naphthalene-1,5-disulfonate having a melting point of 185° to 187° C.

These crystals were recrystallized from 95% ethanol, yielding purified crystals having a melting point of 190° to 192° C.

EXAMPLE 5

5.0 g of α-acetoxy-α-methylacetic acid trimethylammonioethyl ester chloride was dissolved in 5 ml of anhydrous ethanol at 65° C. Into this solution, 4.9 g of naphthalene-1,5-disulfonic acid bistriethylamine salt dissolved in 45 ml of anhydrous ethanol was added dropwise at 65° C. A seed crystal was then added to the resulting solution, which was cooled to 20° C. with stirring.

After stirring for one hour at 20° C., the precipitated crystals were collected by filtration, washed twice with 15 ml of ethanol, and then dried to obtain 6.72 g (yield 93%) of bis-(α-acetoxy-α-methylacetic acid trimethylammonioethyl ester) naphthalene-1,5-disulfonate having a melting point of 188° to 190° C. These crystals were recrystallized from 97% ethanol, yielding purified crystals having a melting point of 190° to 192° C.

What we claim is:

1. A process for producing bischoline-disulfonate derivatives represented by Formula (I):

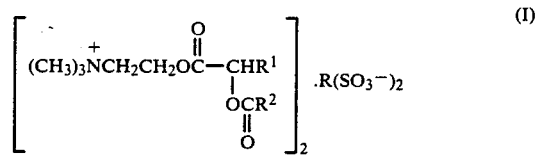
(I)

wherein $R^1$ and $R^2$ each represent a lower alkyl group and R is a naphthalene group, which comprises reacting a trimethylammonium salt derivative represented by Formula (II):

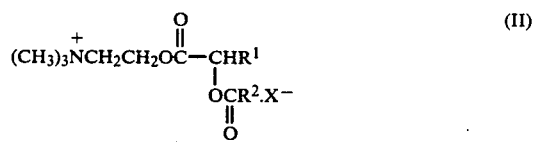
(II)

wherein X is a removable group taken from the class consisting of halogens, sulfonic acid residues, alkylsulfuric acid residues, and alkylphosphate residues; with a disulfonic acid represented by Formula (III):

(III)

in the presence of a lower aliphatic alcohol.

2. The process of claim 1 wherein said sulfonic acid residue is selected from acid residues of methanesulfonic acid, ethanesulfonic acid, benzenesulfonic acid, toluene-2-sulfonic acid, toluene-4-sulfonic acid, naphthalene-1-sulfonic acid, naphthalene-2-sulfonic acid and phenylmethanesulfonic acid; said alkylsulfuric acid residue is selected from acid residues of methylsulfuric acid and ethylsulfuric acid; and said alkylphosphate residue is a dimethylphosphate residue.

3. The process of claim 1 wherein said lower aliphatic alcohol is selected from ethanol, propanol, isopropanol, and butanol.

4. The process of claim 3 wherein said alcohol is selected from ethanol and isopropanol.

5. The process of claim 1 wherein the v/w ratio, milliliters to grams, of said solvent to said compound of Formula (II) is from 4:1 to 20:1.

6. The process of claim 1 wherein said disulfonic acid is present in an amount not greater than 1 equivalent per equivalent of the compound of said Formula (II).

7. The process of claim 1 further comprising maintaining a reaction temperature of about 5° to about 80° C.

8. The process of claim 1 wherein said reacting step takes place over a period of about 5 minutes to about 2 hours.

9. The process of claim 1 wherein said disulfonic acid is present in an amount not greater than 1 equivalent per equivalent of the compound of said Formula (II), said reacting step takes place between a temperature of about 5° and about 80° C., said reacting step takes place over a period of about 5 minutes to about 2 hours, and the ratio, milliliters to grams of said solvent to said compound of said Formula (II) is from 4:1 to 20:1.

* * * * *